United States Patent [19]
Bullock et al.

[11] Patent Number: 6,165,419
[45] Date of Patent: Dec. 26, 2000

[54] REGISTER SCENTING SYSTEM

[76] Inventors: David Bullock; Corrinthia Bullock, both of 1743 Noble St., Gary, Ind. 46404

[21] Appl. No.: 09/195,956
[22] Filed: Nov. 19, 1998
[51] Int. Cl.[7] ........................................... C01F 1/00
[52] U.S. Cl. ................. 422/124; 239/57; 239/60; 422/122
[58] Field of Search ................ 422/5, 122, 124; 239/57, 60

[56] References Cited

U.S. PATENT DOCUMENTS

| 4,617,157 | 10/1986 | Stein et al. | 422/124 |
| 4,840,773 | 6/1989 | Wade | 422/124 |
| 5,368,822 | 11/1994 | McNeil | 422/124 |
| 5,478,505 | 12/1995 | McElfresh et al. | 422/124 |
| 5,547,636 | 8/1996 | Vick et al. | 422/124 |

*Primary Examiner*—Krisanne Thornton

[57] ABSTRACT

A scented air register system is provided including a vent assembly with a plurality of louvers mounted thereon. Also included is a scenting container coupled to the vent assembly and depending therefrom. Next provided is a lid assembly mounted over the scenting container and being accessible from above the vent assembly.

7 Claims, 2 Drawing Sheets

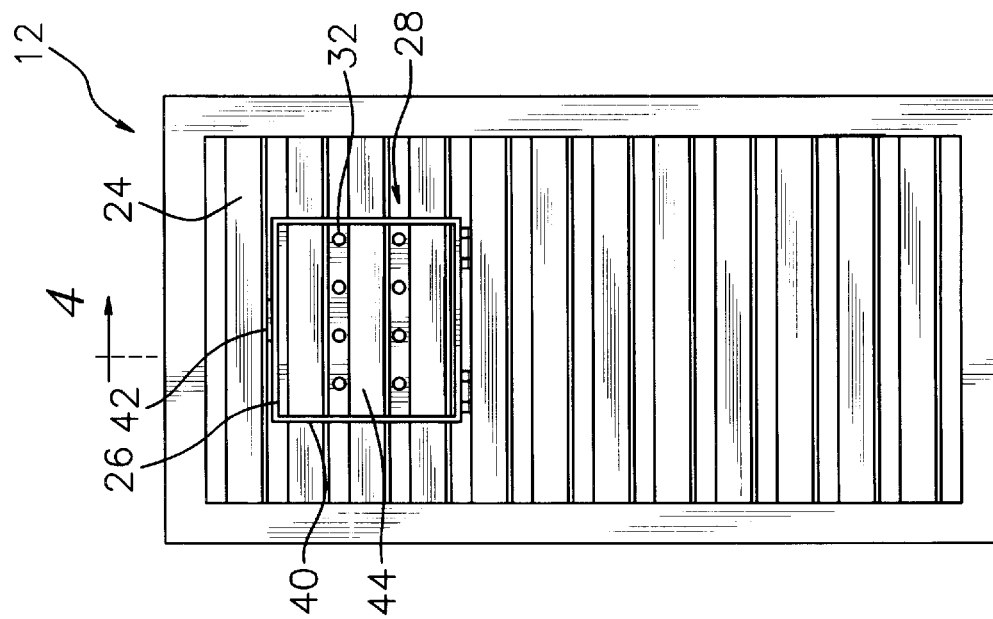
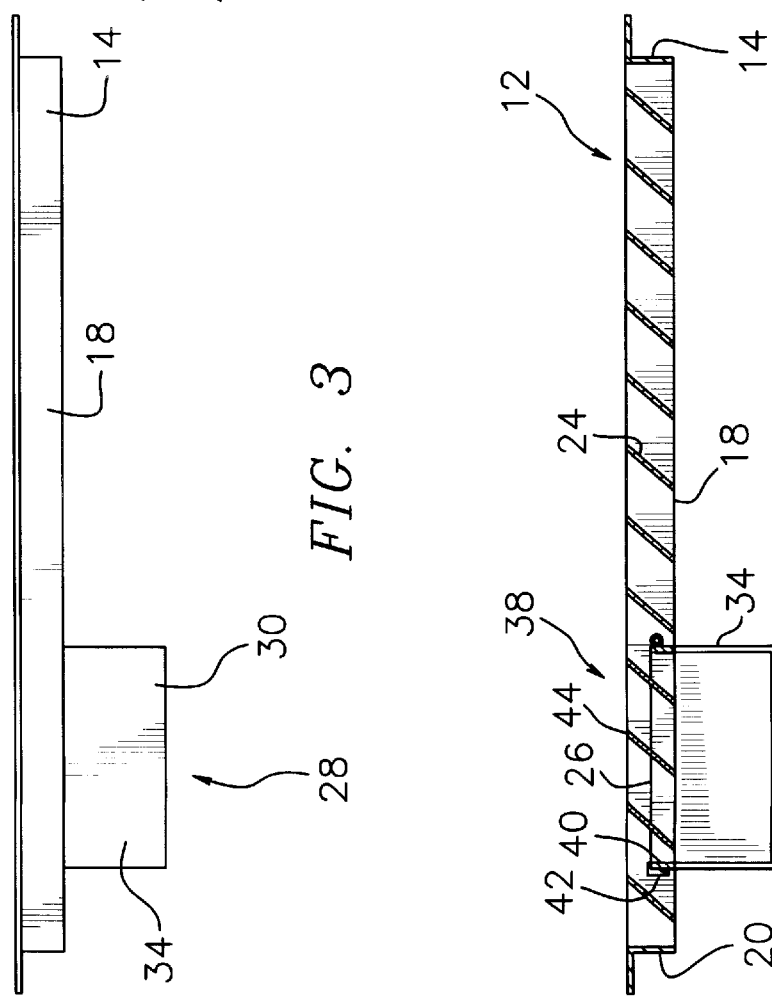
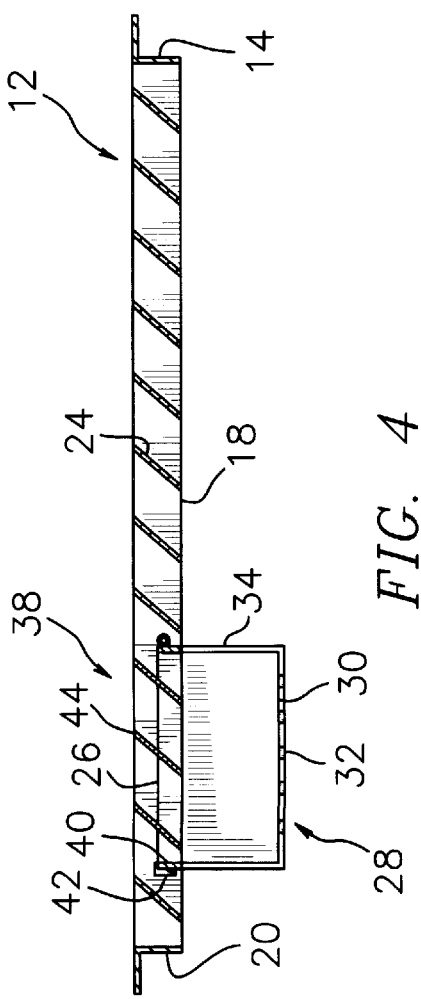

REGISTER SCENTING SYSTEM

BACKGROUND OF THE INVENTION

1. Field of the Invention

The present invention relates to scenting devices and more particularly pertains to a new register scenting system for scenting a building with a scenting material positioned within registers.

2. Description of the Prior Art

The use of scenting devices is known in the prior art. More specifically, scenting devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,368,822; 5,141,707; 5,240,487; 4,903,584; 3,443,906; and U.S. Pat. No. Des. 288,713.

In these respects, the register scenting system according to the present invention substantially departs from the conventional concepts and designs of the prior art, and in so doing provides an apparatus primarily developed for the purpose of scenting a building with a scenting material positioned within registers.

SUMMARY OF THE INVENTION

In view of the foregoing disadvantages inherent in the known types of scenting devices now present in the prior art, the present invention provides a new register scenting system construction wherein the same can be utilized for scenting a building with a scenting material positioned within registers.

The general purpose of the present invention, which will be described subsequently in greater detail, is to provide a new register scenting system apparatus and method which has many of the advantages of the scenting devices mentioned heretofore and many novel features that result in a new register scenting system which is not anticipated, rendered obvious, suggested, or even implied by any of the prior art scenting devices, either alone or in any combination thereof.

To attain this, the present invention generally comprises a vent assembly having a frame with a plurality of walls each residing within a unique vertical plane. Such walls include a pair of planar rectangular elongated side walls and a pair of planar rectangular short end walls, as shown in FIGS. 1–3. Further, the frame further includes a peripheral flange coupled to a top edge of the frame. This peripheral flange extends outwardly from the frame within a horizontal plane in order to be mounted within a vent opening. The vent assembly further has a plurality of louvers each having a planar rectangular configuration. The louvers are equipped with ends being coupled between the side walls of the frame. Ideally, the louvers remain angled within parallel planes, as shown in FIG. 4. For reasons that will soon become apparent, a portion of the louvers adjacent one of the end faces of the frame have a square cut out. As shown in FIG. 1, the louvers adjacent to the cut out terminate at about ¼ a length thereof from the frame. Next provided is a scenting container including a planar square bottom face with a matrix of apertures formed therein. The scenting container further has a peripheral side wall integrally coupled to a periphery of the bottom face and extending upwardly therefrom. By this structure, an interior space, an open top and an upper peripheral edge are defined. The upper peripheral edge of the peripheral side wall is preferably fixed within the cut out of the vent assembly between the terminations of the louvers. Finally, a lid assembly is provided including a peripheral lid support with a square configuration defined by four interconnected bars. Together, these bars have a cross-section similar to that of the peripheral side wall of the scenting container. A first one of the bars of the peripheral lid support of the lid assembly is hingably coupled to the upper peripheral edge of the scenting container. A second one of the bars of the peripheral lid support has a latch for releasably engaging the upper peripheral edge of the scenting container, as shown in FIG. 4. The peripheral lid support further comprises a plurality of louver sections mounted between a third and fourth one of the bars thereof. As such, the louver sections remain in alignment with the louvers of the vent assembly when the lid assembly is closed. Further, the peripheral lid support allows access to the scenting container when the lid assembly is open. When open, potpourri may be removably situated within the scenting container for the purpose of scenting air flowing through the bottom face of the scenting container and through the louver sections of the lid assembly.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new register scenting system apparatus and method which has many of the advantages of the scenting devices mentioned heretofore and many novel features that result in a new register scenting system which is not anticipated, rendered obvious, suggested, or even implied by any of the prior art scenting devices, either alone or in any combination thereof.

It is another object of the present invention to provide a new register scenting system which may be easily and efficiently manufactured and marketed.

It is a further object of the present invention to provide a new register scenting system which is of a durable and reliable construction.

An even further object of the present invention is to provide a new register scenting system which is susceptible of a low cost of manufacture with regard to both materials and labor, and which accordingly is then susceptible of low prices of sale to the consuming public, thereby making such register scenting system economically available to the buying public.

Still yet another object of the present invention is to provide a new register scenting system which provides in the apparatuses and methods of the prior art some of the advantages thereof, while simultaneously overcoming some of the disadvantages normally associated therewith.

Still another object of the present invention is to provide a new register scenting system for scenting a building with a scenting material positioned within registers.

Even still another object of the present invention is to provide a new register scenting system that includes a vent assembly with a plurality of louvers mounted thereon. Also included is a scenting container coupled to the vent assembly and depending therefrom. Next provided is a lid assembly mounted over the scenting container and being accessible from above the vent assembly.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a top view of the present invention.

FIG. 3 is a side view of the present invention.

FIG. 4 is a side cross-sectional view of the present invention taken along line 4—4 shown in FIG. 2.

DESCRIPTION OF THE PREFERRED EMBODIMENT

Figure 1:
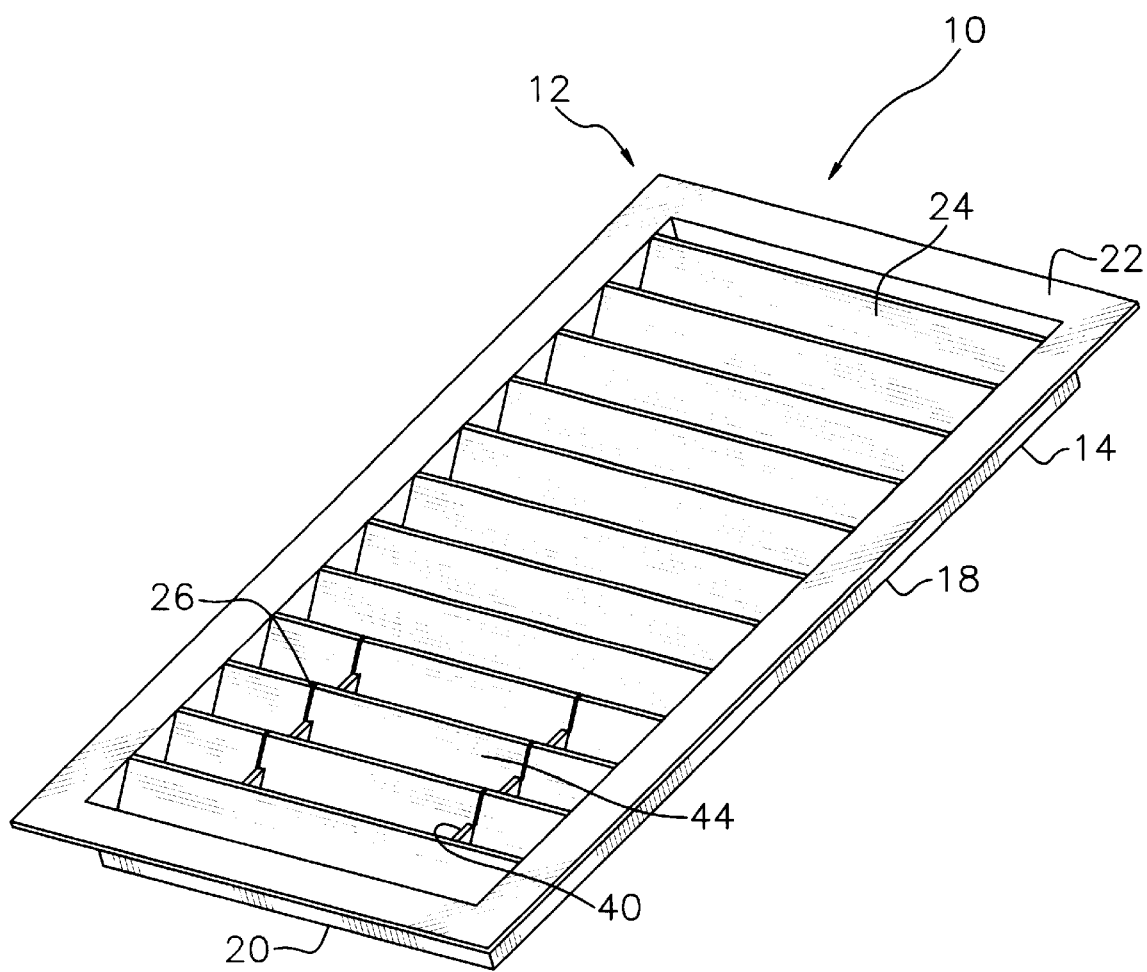
FIG. 1 is a perspective view of a new register scenting system according to the present invention.

With reference now to the drawings, and in particular to FIGS. 1 through 4 thereof, a new register scenting system embodying the principles and concepts of the present invention and generally designated by the reference numeral 10 will be described.

The present invention, designated as numeral 10, includes a vent assembly 12 having a frame 14 with a plurality of walls 16 each residing within a unique vertical plane. Such walls include a pair of planar rectangular elongated side walls 18 and a pair of planar rectangular short end walls 20, as shown in FIGS. 1–3. Further, the frame further includes a peripheral flange 22 coupled to a top edge of the frame. This peripheral flange extends outwardly from the frame within a horizontal plane in order to be mounted within a vent opening formed in a floor of a structure.

The vent assembly further has a plurality of louvers 24 each having a planar rectangular configuration. The louvers are equipped with ends being coupled between the side walls of the frame. Ideally, the louvers remain angled within parallel planes, as shown in FIG. 4. For reasons that will soon become apparent, a portion of the louvers adjacent one of the end faces of the frame have a square cut out 26 formed therein. As shown in FIG. 1, the louvers adjacent to the cut out terminate at about ¼ a length thereof from the frame. Ideally, the cut out has a length of about ⅓ that of the vent assembly.

Next provided is a scenting container 28 including a planar square bottom face 30 with a matrix of apertures 32 formed therein. The scenting container further has a peripheral side wall 34 integrally coupled to a periphery of the bottom face and extending upwardly therefrom. By this structure, an interior space, an open top and an upper peripheral edge are defined. The upper peripheral edge of the peripheral side wall is preferably fixed within the cut out of the vent assembly between the terminations of the louvers.

The coupling between the scenting container and vent assembly may be accomplished by any desired method. For example, the upper peripheral edge of the scenting container may be equipped with a pair of outwardly extending arms for being attached to lower edges of the short louvers of the vent. As an option, such arms may also extend all the way to lower edges of the side walls of the frame of the vent assembly.

Finally, a lid assembly 38 is provided including a peripheral lid support 40 with a square configuration defined by four interconnected bars. Together, these bars have a cross-section similar to that of the peripheral side wall of the scenting container. A height of the peripheral lid support is preferably less than ¼ that of the scenting container. A first one of the bars of the peripheral lid support of the lid assembly is hingably coupled to the upper peripheral edge of the scenting container. A second one of the bars of the peripheral lid support has a latch 42 for releasably engaging the upper peripheral edge of the scenting container, as shown in FIG. 4. Ideally, the latch depends downwardly from the peripheral lid support and frictionally engages the peripheral side wall of the scenting container.

The peripheral lid support further comprises a plurality of louver sections 44 mounted between a third and fourth one of the bars thereof. As such, the louver sections remain in alignment with the louvers of the vent assembly when the lid assembly is closed. Further, the peripheral lid support allows access to the scenting container when the lid assembly is open. When open, potpourri or any other scenting material may be removably situated within the scenting container for the purpose of scenting air flowing through the bottom face of the scenting container and through the louver sections of the lid assembly.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A scented air register system comprising, in combination:

a vent cover assembly including a frame with a plurality of walls, the vent cover assembly having a front side, the walls including a pair of planar rectangular elongated side walls and a pair of planar rectangular short end walls, the frame further including a peripheral flange coupled to a top edge of the walls of the frame and extending outwardly from the top edge in a common plane, the vent cover assembly further including a plurality of louvers each having a planar rectangular configuration with ends being coupled to the side walls and extending between the side walls of the frame, the louvers being oriented at an acute angle with respect to the common plane of the peripheral flange, the louvers lying in parallel planes to each other, wherein a portion of each of three adjacent louvers have a square cut out such that the three louvers adjacent to the cut out terminate at a length of about ¼ of the distance between the side walls;

a scenting container for scenting air moving through the vent cover assembly, the scenting container including a planar square bottom wall with a matrix of apertures formed therein, a peripheral side wall integrally coupled to a periphery of the bottom wall and extending perpendicularly from the bottom wall to define an interior space, the peripheral side wall having an open top and an upper peripheral edge, the upper peripheral edge of the peripheral side wall being positioned in the cut out of the vent cover assembly and being mounted on the terminations of the three louvers; and a lid assembly including a peripheral lid support with a square configuration, the peripheral lid support being defined by four interconnected bars having a cross-section similar to that of the peripheral side wall of the scenting container, a first one of the bars of the peripheral lid support of the lid assembly being pivotally mounted on the upper peripheral edge of the scenting container such that the peripheral lid support is pivotable between an operational orientation with the peripheral lid support located adjacent the upper peripheral edge of the scenting container and a refill orientation with the peripheral lid support being pivoted away from the upper peripheral edge of the scenting container through the common plane for permitting refilling of the interior space of the scenting container with a scenting material from the front side of the vent cover assembly, a second one of the bars of the peripheral lid support opposite of the first bar having a latch for releasably engaging the upper peripheral edge of the scenting container, the peripheral lid support further including a plurality of louver sections mounted between a third and fourth one of the bars thereof such that the louver sections are alignable with the louvers of the vent cover assembly when the lid assembly is in a closed position and further allow access to the scenting container when the lid assembly is in the refill orientation.

2. A scented air register system comprising:

a vent cover assembly with a plurality of louvers mounted thereon, the vent cover assembly having a front side for orienting toward a living space, the vent cover assembly having a plurality of louvers, a portion of at least two of the louvers being cut out;

a scenting container mounted on the vent cover assembly for scenting air moving through the vent cover assembly, the scenting container having an open top and an upper peripheral edge, the upper peripheral edge of the peripheral side wall being positioned in the cut out of the louvers of the vent cover assembly; and a lid assembly mounted over the scenting container and being accessible from above the vent assembly, a lid assembly including a peripheral lid support, the peripheral lid support of the lid assembly being pivotally mounted with respect to the upper peripheral edge of the scenting container such that the peripheral lid support is pivotable between an operational orientation with the peripheral lid support located adjacent the upper peripheral edge of the scenting container and a refill orientation with the peripheral lid support being pivoted away from the upper peripheral edge of the scenting container through the front side of the vent cover assembly for permitting refilling of the interior space of the scenting container with a scenting material from the front side of the vent cover assembly.

3. A scented air register system as set forth in claim 2 wherein the lid assembly allows air to pass therethrough.

4. A scented air register system as set forth in claim 3 wherein the lid assembly includes a plurality of louvers similar to those of the vent assembly.

5. A scented air register system as set forth in claim 4 wherein the louvers of the lid assembly remain in alignment with those of the vent assembly when in a closed orientation.

6. A scented air register system as set forth in claim 2 wherein the lid assembly includes a latch for engaging the scenting container when in a closed orientation.

7. A scented air register system as set forth in claim 2 wherein the scenting container includes a plurality of apertures formed in a bottom face thereof.

* * * * *